(12) United States Patent
Fujioka et al.

(10) Patent No.: US 8,257,331 B2
(45) Date of Patent: Sep. 4, 2012

(54) ABSORBENT PRODUCT

(75) Inventors: Masaru Fujioka, Mima-gun (JP); Yuki Takahashi, Mima-gun (JP)

(73) Assignee: Livedo Corporation, Ehime (JP)

( * ) Notice: Subject to any disclaimer, the term of this patent is extended or adjusted under 35 U.S.C. 154(b) by 811 days.

(21) Appl. No.: 12/153,257

(22) Filed: May 15, 2008

(65) Prior Publication Data

US 2008/0300568 A1 Dec. 4, 2008

(30) Foreign Application Priority Data

May 30, 2007 (JP) ................. P2007-143494

(51) Int. Cl.
*A61F 13/15* (2006.01)
*A61F 13/20* (2006.01)

(52) U.S. Cl. .......... 604/385.24; 604/385.27; 604/385.01

(58) Field of Classification Search ...... 4/385.22–285.3, 4/396, 367, 378, 385.01; 604/385.22–385.3, 604/396, 367, 378, 385.01
See application file for complete search history.

(56) References Cited

U.S. PATENT DOCUMENTS

| | | | |
|---|---|---|---|
| 4,655,760 | A | 4/1987 | Morman et al. |
| 5,634,917 | A | 6/1997 | Fujioka et al. |
| 5,735,839 | A | 4/1998 | Kawaguchi et al. |
| 6,287,169 | B1 * | 9/2001 | Willms et al. ............. 450/101 |
| 6,423,042 | B1 | 7/2002 | Sasaki |
| 7,150,731 | B2 * | 12/2006 | Cazzato et al. ........ 604/385.27 |
| 2002/0049421 | A1 * | 4/2002 | Hayase et al. ........ 604/385.27 |
| 2002/0072728 | A1 | 6/2002 | Shinohara et al. |
| 2004/0030317 | A1 | 2/2004 | Torigoshi |
| 2005/0131373 | A1 | 6/2005 | Wright et al. |
| 2008/0071241 | A1 * | 3/2008 | Bittner et al. ........ 604/385.27 |
| 2009/0240229 | A1 | 9/2009 | Malowaniec |
| 2011/0125126 | A1 | 5/2011 | Malowaniec |

FOREIGN PATENT DOCUMENTS

| | | |
|---|---|---|
| EP | 1 153 585 | 11/2001 |
| EP | 1 208 827 * | 5/2002 |
| EP | 1 761 224 | 11/2007 |
| EP | 1 997 463 | 12/2008 |
| JP | 8-112308 | 5/1996 |
| JP | 2000-140021 | 5/2000 |

(Continued)

OTHER PUBLICATIONS

European Search Report (in English language) issued Sep. 17, 2008.

(Continued)

*Primary Examiner* — Michele M Kidwell
(74) *Attorney, Agent, or Firm* — Wenderoth, Lind & Ponack, L.L.P.

(57) ABSTRACT

In a pants-type absorbent product, a first middle elastic member is located along a horizontal direction in a middle front part between a pair of leg openings in an outer covering sheet. The first middle elastic member contracts a first sheet and a second sheet, and middle gathers are formed. Thus, it is possible to improve fitting of a middle part to a wearer. In the middle front part, both ends of the first middle elastic member are apart from edges of the pair of leg openings, and a pair of non-contracted parts are provided between the both ends of the first middle elastic member and the edges of the pair of leg openings, to thereby improve flexibility of portions in the vicinities of the leg openings in the outer covering sheet.

19 Claims, 9 Drawing Sheets

FOREIGN PATENT DOCUMENTS

| | | |
|---|---|---|
| JP | 3286607 | 5/2002 |
| JP | 2002-172132 | 6/2002 |
| JP | 2005-21708 | 1/2005 |
| JP | 2005-278774 | 10/2005 |
| JP | 2008-148941 | 7/2008 |
| WO | 2006/000303 | 1/2006 |
| WO | 2007/000315 | 1/2007 |

OTHER PUBLICATIONS

Extended European Search Report issued Aug. 9, 2011 in European Application No. 11 00 5282.6.

* cited by examiner

ABSORBENT PRODUCT

BACKGROUND OF THE INVENTION

1. Field of the Invention

The present invention relates to a pants-type absorbent product which has a waist opening at an upper end and a pair of leg openings on a lower part.

2. Description of the Background Art

In a disposal diaper for receiving excrement from a wearer, elasticity has been conventionally applied to various portions in order to improve fitting to the wearer or improve an appearance of the disposal diaper.

In a pants-type disposal diaper disclosed in Japanese Patent Application Laid-Open No. 2002-172132 (Document 1), contracted members parallel to a waist opening are continuously provided from right and left leg opening edges to positions close to an absorbent core (or to a position corresponding the absorbent core), and the leg opening edges in an outer form sheet thereby contract toward the central side in a width direction of the disposal diaper, to prevent the leg opening edges from fluttering and enhance an appearance around legs of the disposal diaper.

Japanese Patent Application Laid-Open No. 8-112308 (Document 2) discloses a pants-type disposal diaper where a waist opening portion and a pair of leg opening portions are provided with an elastic member forming continuous gathers around the entire circumference of each of the peripheral edges, and a body-surrounding portion between the waist opening portion and the pair of leg opening portions is provided with an elastic member forming continuous gathers around almost the whole of the body-surrounding portion. In the disposal diaper, a crotch region of a front part, the crotch region being a urination point, is provided with a plurality of elastic members extending from one opening edge of the pair of leg opening portions to the other opening edge, and continuous gathers are formed in the urination point toward a width direction of the disposal diaper, to thereby improve fitting in the urination point.

In the disposal diaper of Document 1, since portions in the vicinities of the leg opening edges in the outer sheet are gathered toward the central portion in the width direction by contracting the elastic members provided in the leg opening edges, there is a possibility that the legs of a wearer are strongly compressed by decreasing flexibility of the portions in the vicinities of the leg opening edges. The legs of the wearer might not be smoothly inserted into leg openings in wearing the disposal diaper, which decreases the comfort of the wearer. Further, there is a possibility that the appearance of the disposal diaper is reduced by drawing the leg opening edges toward the center in the width direction.

In the disposal diaper of Document 2, the elastic members provided around the entire circumferences of the pair of leg opening portions and the elastic members provided in the urination point cross each another in the vicinities of the leg openings, and fitting of the portions in the vicinities of the leg openings are decreased in crossing portions of these elastic members, which decreases the comfort of a wearer in wearing the disposal diaper.

SUMMARY OF THE INVENTION

The present invention is intended for a pants-type absorbent product which has a waist opening at an upper end and a pair of leg openings on a lower part. It is an object of the present invention to improve fitting of a middle part between the pair of leg openings to a wearer, and to improve flexibility of portions in the vicinities of the leg openings.

The pants-type absorbent product comprises: an outer covering sheet folded in a middle part which is a lower part between a front part and a back part to be positioned on a stomach side and a back side of a wearer, right and left ends of the front part being bonded to right and left ends of the back part, respectively, to form a waist opening at upper ends of the front part and the back part and a pair of leg openings on right and left sides of the middle part; and an absorbent which is attached on an inner side of the outer covering sheet to absorb excrement from the wearer, and in the absorbent product, the outer covering sheet comprises: a first sheet; a second sheet which is laminated on the first sheet to be bonded with the first sheet; and a middle elastic member interposed between the first sheet and the second sheet in the middle part, extending from one leg opening to the other leg opening, and contracting the first sheet and the second sheet to form middle gathers, and both ends of the middle elastic member are at least partially apart from the pair of leg openings, and a pair of non-contracted parts are provided between the both ends of the middle elastic member and the pair of leg openings. It is thereby possible to improve fitting of the middle part to the wearer, and to improve flexibility of portions in the vicinities of the leg openings.

According to a preferred embodiment of the present invention, the middle elastic member has a plurality of elastic yarns, and the both ends of the middle elastic member are both ends of the plurality of elastic yarns.

According to another preferred embodiment of the present invention, the plurality of elastic yarns are formed by cutting both end portions of at least part of extended elastic yarns, which are bonded with the first sheet and the second sheet, together with at least one of the first sheet and the second sheet, to lose elasticity of the both end portions in the pair of non-contracted parts. This makes it possible to easily form the absorbent product.

Preferably, the outer covering sheet further comprises leg elastic members which are located along edges of the pair of leg openings, respectively, and the leg elastic members contract to form a pair of leg opening gathers, and the leg elastic members are formed by cutting extended elastic members, which are bonded with the first sheet and the second sheet, together with at least one of the first sheet and the second sheet, to lose elasticity of portions in the pair of non-contracted parts. It is thereby possible to achieve fitting and flexibility of the portions in the vicinities of the leg openings to the wearer.

More preferably, at least part of extended elastic yarns to be at least part of the middle elastic member and the extended elastic members to be the leg elastic members, are cut in the pair of non-contracted parts with crossing each other.

According to still another preferred embodiment of the present invention, a total width in a horizontal direction of the pair of non-contracted parts is equal to or larger than 20% and equal to or smaller than 60% of a width in the horizontal direction of the middle part at a position where the pair of non-contracted parts are provided, in a state where the outer covering sheet is expanded. According to still another preferred embodiment of the present invention, the middle elastic member is continuous between the pair of non-contracted parts.

According to still another preferred embodiment of the present invention, the middle elastic member is located between the front part and a folded part which is a lower end of the middle part, another middle elastic member is located between the back part and the folded part of the middle part, another middle elastic member is interposed between the first sheet and the second sheet in the middle part, extends from one leg opening to the other leg opening, and contracts the first sheet and the second sheet to form middle gathers, both ends of another middle elastic member are at least partially apart from the pair of leg openings, and another pair of non-contracted parts are provided between the both ends of another middle elastic member and the pair of leg openings.

These and other objects, features, aspects and advantages of the present invention will become more apparent from the following detailed description of the present invention when taken in conjunction with the accompanying drawings.

DETAILED DESCRIPTION OF THE INVENTION

Figure 1:
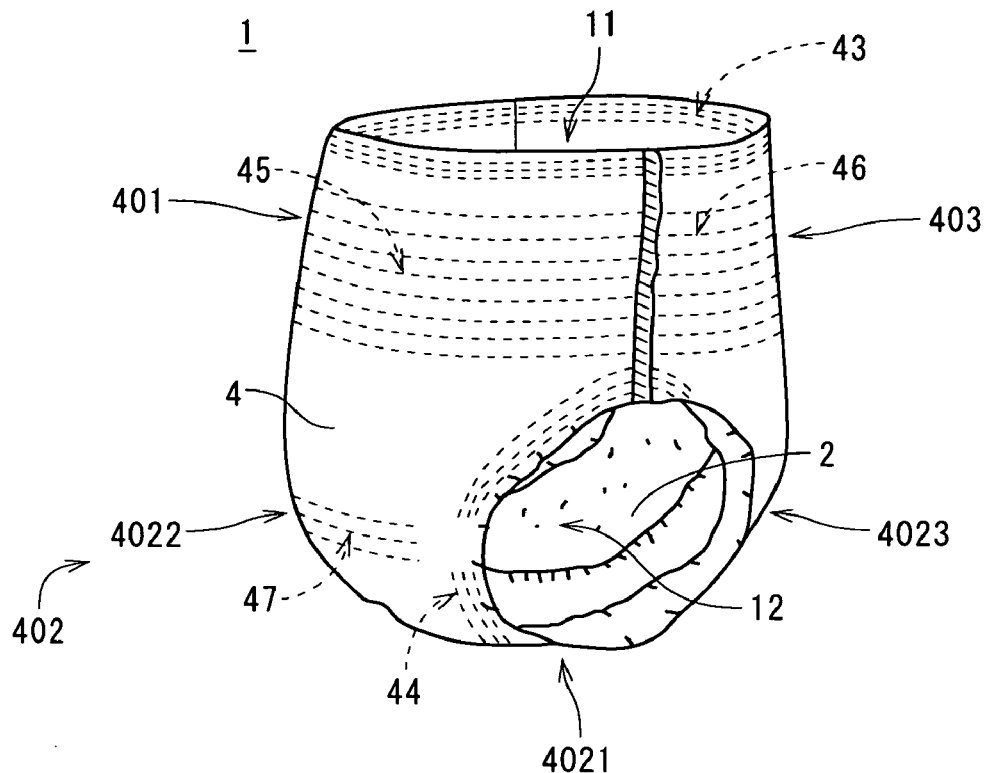
FIG. 1 is a perspective view showing an appearance of an absorbent product in accordance with the first preferred embodiment.
Figure 2:
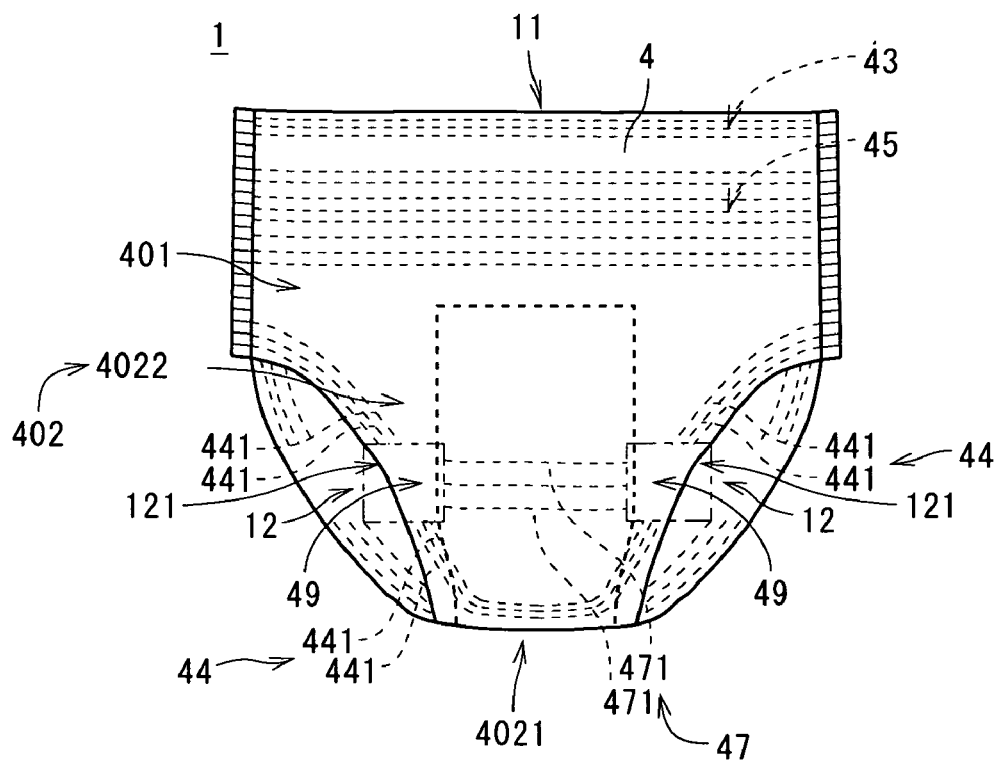
FIG. 2 is a front view of the absorbent product.
Figure 3:
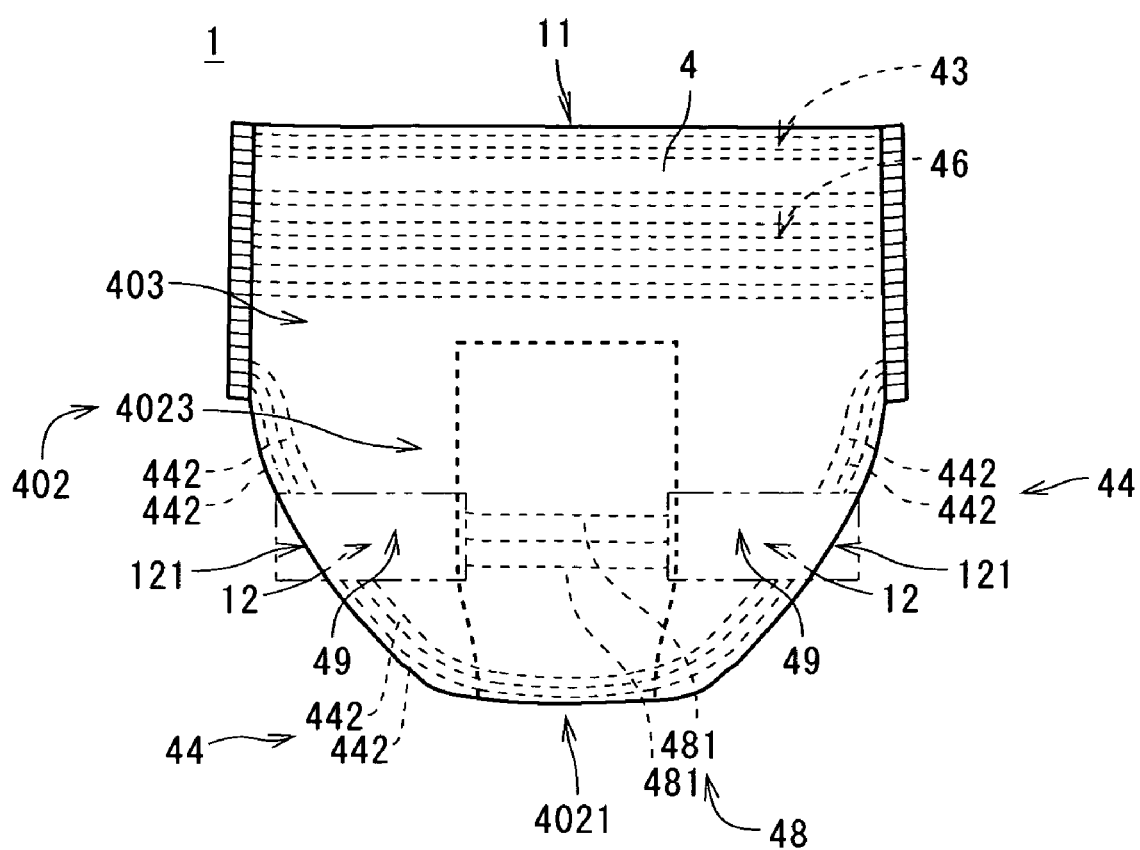
FIG. 3 is a rear view of the absorbent product.

FIG. 1 is a perspective view showing an appearance of an absorbent product 1 in accordance with the first preferred embodiment of the present invention. FIG. 2 is a front view (i.e., view of a portion to be positioned on a stomach side (an abdomen) of a wearer) of the absorbent product 1 and FIG. 3 is a rear view (i.e., view of a portion to be positioned on a back side (a back) of the wearer) of the absorbent product 1. As shown in FIGS. 1 to 3, the absorbent product 1 is a pants-type (i.e., pull-up type) disposal diaper which has a waist opening 11 at an upper end (i.e., an end on the upper side of FIG. 1) and a pair of leg openings 12 on a lower part.

Figure 4:
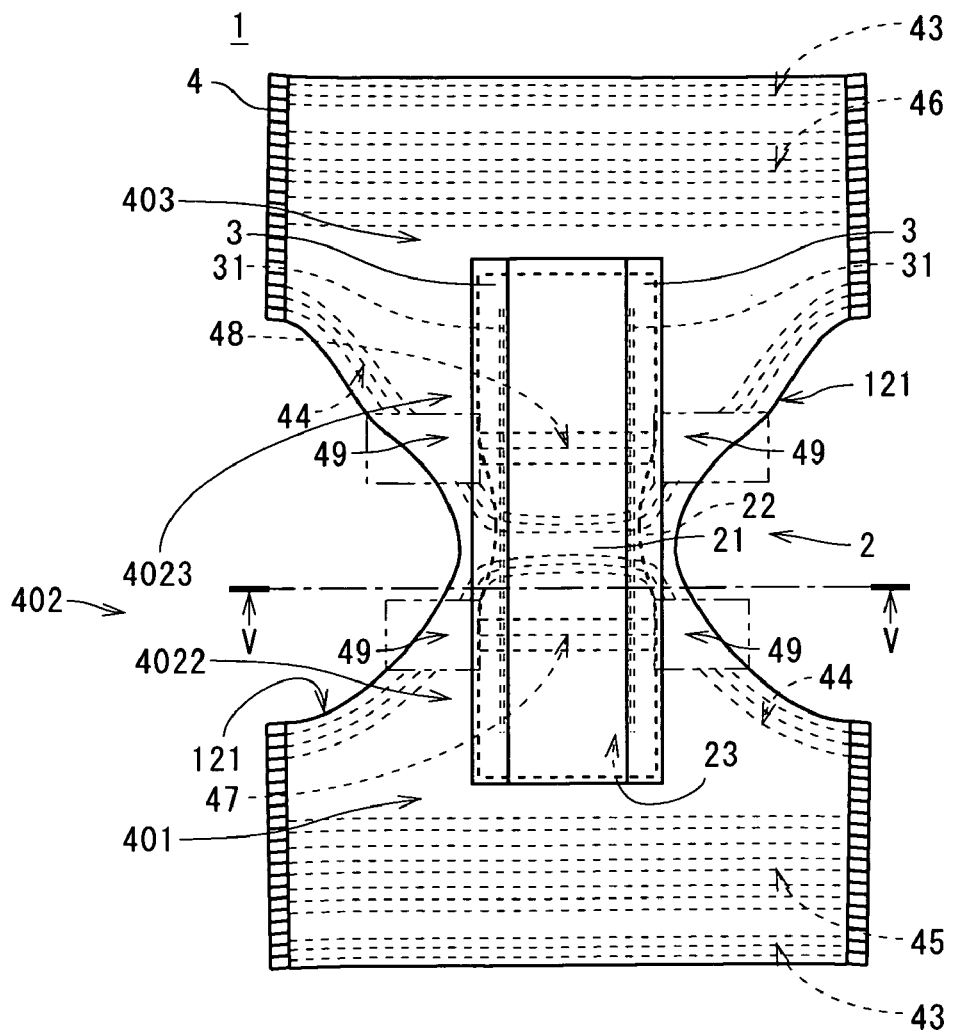
FIG. 4 is a plan view of the absorbent product in a state where the absorbent product is spread.

FIG. 4 is a plan view of the absorbent product 1 as viewed from the wearer's side in a state where the absorbent product 1 is spread. As shown in FIG. 4, the absorbent product 1 has an almost sheet-like outer covering sheet 4 and an absorbent 2 which is attached on an inner side of the outer covering sheet 4 to absorb excrement from the wearer. In the absorbent product 1, a lower portion 401 in FIG. 4 of the outer covering sheet 4 is to be positioned on the stomach side of the wearer, and an upper portion 403 in FIG. 4 is to be positioned on the back side of the wearer. In the following description, the portions 401, 403 which are to be positioned on the stomach side and the back side of the wearer in the outer covering sheet 4 are referred to as a "front part 401" and a "back part 403", respectively, and a portion 402 to come into contact with a crotch region of the wearer between the front part 401 and the back part 403 is referred to as a "middle part 402".

As shown in FIG. 1, in the absorbent product 1, the outer covering sheet 4 is folded in a folded part 4021 which is a lower end of the middle part 402, together with the absorbent 2. Right and left ends of the front part 401 (i.e., both ends in a width direction of the front part 401) are bonded to right and left ends of the back part 403 (i.e., both ends in the width direction of the back part 403), respectively. Thus, the waist opening 11 is formed at upper ends of the front part 401 and the back part 403 and a pair of leg openings 12 are formed on right and left sides of the middle part 402, to thereby form the absorbent product 1 in a shape of underpants. In the following description, a portion between the front part 401 and the folded part 4021 of the middle part 402 is referred to as a "middle front part 4022" and a portion between the back part 403 and the folded part 4021 of the middle part 402 is referred to as a "middle back part 4023".

Figure 5:
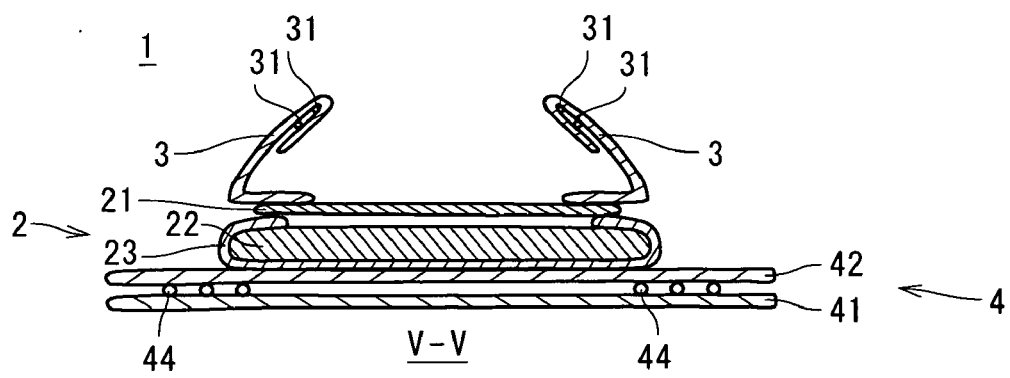
FIG. 5 is a cross-sectional view of the absorbent product.

FIG. 5 is a cross-sectional view of the absorbent product 1 taken along a line V-V in FIG. 4. As shown in FIGS. 4 and 5, the absorbent 2 has an absorbent core 22, a top sheet 21 covering a main surface on an inner side of the absorbent core 22, a back sheet 23 covering a main surface on an outer side of the absorbent core 22 (opposite to the wearer side), and a pair of side wall parts 3 which are provided over an almost entire length in a longitudinal direction of the absorbent core 22 on right and left sides in the width direction (i.e., horizontal direction) of the absorbent core 22 (i.e., the longitudinal direction is a vertical direction in FIG. 4 and corresponds to a longitudinal direction of the absorbent product 1, and the width direction is perpendicular to the longitudinal direction of the absorbent core 22). The contour of the absorbent core 22 is shown by a thick broken-line in FIG. 4. The top sheet 21 and the back sheet 23 are bonded each other around the absorbent core 22 by hot melt adhesive or the like, and the side wall part 3 is bonded to each side of the absorbent core 22. In FIG. 5, a space is provided between the top sheet 21 and the absorbent core 22 for convenience of illustration.

The top sheet 21 is a nonwoven fabric made of liquid-pervious material, for example, hydrophilic fiber, and the top sheet 21 immediately catches moisture of excrement from the wearer and moves the moisture into the absorbent core 22. Examples of the nonwoven fabric used for the top sheet 21 are a point-bond nonwoven fabric, air-through nonwoven fabric, or spunlace nonwoven fabric, and as hydrophilic fibers for making these nonwoven fabrics, normally, cellulose, rayon, cotton or the like are used. As the top sheet 21, a liquid-pervious nonwoven fabric made of hydrophobic fiber (for example, polypropylene, polyethylene, polyester, polyamide, or nylon) on which hydrophilic treatment is performed with a surfactant may be utilized or a microporous plastic film may be used.

The absorbent core 22 is formed by wrapping a mixture of hydrophilic fibers (e.g., crushed pulp fibers or cellulose fibers) and granulated absorbent polymers (e.g., SAP (Super Absorbent Polymer)) in a cover sheet such as a tissue paper or a liquid-pervious nonwoven fabric, and the absorbent core 22 rapidly absorbs and retains moisture passing through the top sheet 21. The cover sheet is bonded to the hydrophilic fibers and the absorbent polymers with the hot melt adhesive, to prevent deformation of the hydrophilic fibers and falling of the absorbent polymers (especially, falling after absorption of moisture).

The back sheet 23 is a water-repellent or liquid-impervious plastic film, and the back sheet 23 prevents the moisture which has passed through the top sheet 21 and the moisture which is retained in the absorbent core 22 from leaking out into the outer covering sheet 4. From the view point of comfort for wearer, it is preferable that a plastic film with breathability is used as the back sheet 23. As the back sheet 23, a water-repellent or liquid-impervious nonwoven fabric or a laminated sheet in which a water-repellent or liquid-impervious plastic film is laminated on an inner side of the water-repellent or liquid-impervious nonwoven fabric can be used. Nonwoven fabrics used for the back sheet 23 are, for example, a spunbond nonwoven fabric, a meltblown nonwoven fabric, or a SMS (spunbond-meltblown-spunbond) nonwoven fabric, on which water-repellent treatment may be applied as necessary.

As shown in FIGS. 4 and 5, two elastic yarns 31 extending in the longitudinal direction are bonded to each of the pair of side wall parts 3 and the elastic yarns 31 are extended in the expanded absorbent product 1 shown in FIG. 4. In the absorbent product 1, the elastic yarns 31 contract to stand up the side wall parts 3 toward the wearer on the right and left sides of the absorbent 2, to form standing gathers which come into contact with the vicinity of wearer's crotch in wearing.

The side wall parts 3 are made of water-repellent or liquid-impervious nonwoven fabric (i.e., spunbond nonwoven fabric, meltblown nonwoven fabric, or SMS nonwoven fabric), plastic film, or combinations of these materials. From the viewpoint of improving comfort of the absorbent product 1, it is preferable that the side wall parts 3 have breathability. As the elastic yarns 31, polyurethane yarn, strip-like polyurethane film, yarn-like or strip-like natural rubber, or the like are used for example.

As shown in FIG. 5, the outer covering sheet 4 has a first sheet 41 and a second sheet 42 which is laminated on the first sheet 41 to be bonded with the first sheet 41 by the hot melt adhesive. In FIG. 5, a space is provided between the first sheet 41 and the second sheet 42 for convenience of illustration. The back sheet 23 of the absorbent 2 is bonded on the second sheet 42 of the outer covering sheet 4 by the hot melt adhesive or the like. The first sheet 41 and the second sheet 42 are water-repellent or liquid-impervious nonwoven fabrics in the present preferred embodiment. Though a water-repellent or liquid-impervious plastic film or a laminated sheet of plastic film and nonwoven fabric may be used as the first sheet 41 and the second sheet 42, it is preferable that the first sheet 41 and the second sheet 42 are formed of nonwoven fabric from the view point of improving feel of the absorbent product 1.

As shown in FIGS. 1 to 3, the outer covering sheet 4 further has a waist elastic member 43 which is located along an edge of the waist opening 11, leg elastic members 44 which are located along edges of the pair of leg openings 12, respectively, a front elastic member 45 and a back elastic member 46 which are located on the front part 401 and the back part 403, respectively, along the horizontal direction (i.e., the width direction) between the waist elastic member 43 and the leg elastic members 44, and a first middle elastic member 47 and a second middle elastic member 48 which are located along the horizontal direction on the middle front part 4022 and the middle back part 4023 in the middle part 402 between the pair of leg openings 12.

As shown in FIG. 5, the leg elastic members 44 are bonded with the first sheet 41 and the second sheet 42 between the first sheet 41 and the second sheet 42, by using the hot melt adhesive or the like. The waist elastic member 43, the front elastic member 45 and the back elastic member 46, and the first middle elastic member 47 and the second middle elastic member 48 shown in FIGS. 1 to 3 are bonded with the first sheet 41 and the second sheet 42 between the first sheet 41 and the second sheet 42 shown in FIG. 5, by using the hot melt adhesive or the like, similarly to the leg elastic members 44.

As shown in FIG. 1, the extended waist elastic member 43 is bonded along the edge of the waist opening 11 around the almost whole waist opening 11. By contracting the waist elastic member 43, the first sheet 41 and the second sheet 42 (see FIG. 5) contract to form waist opening gathers. The extended leg elastic members 44 are bonded along the edges of the pair of leg openings 12, respectively, and by contracting the leg elastic members 44, the first sheet 41 and the second sheet 42 contract to form a pair of leg opening gathers.

The extended front elastic member 45 and the extended back elastic member 46 are bonded on the front part 401 and the back part 403 of the outer covering sheet 4, respectively. By contracting the front elastic member 45 and the back elastic member 46, the first sheet 41 and the second sheet 42 contract to form front gathers and back gathers. The extended first middle elastic member 47 and the extended second middle elastic member 48 shown in FIGS. 2 and 3 are bonded on the middle front part 4022 and the middle back part 4023 of the middle part 402, respectively. By contracting the first middle elastic member 47 and the second middle elastic member 48, the first sheet 41 and the second sheet 42 (see FIG. 5) contract to form middle gathers.

In other words, (a part of) the outer covering sheet 4 which is a part of the absorbent product 1 is an elastic sheet. In the present preferred embodiment, the waist elastic member 43, the leg elastic members 44, the front elastic member 45 and the back elastic member 46, and the first middle elastic member 47 and the second middle elastic member 48 are bonded with the first sheet 41 and the second sheet 42, respectively, in a state where they are preferably extended 1.1 to 5.0 times what they are.

As shown in FIGS. 2 and 4, both ends of the first middle elastic member 47 are apart from edges 121 of the pair of leg openings 12 in the outer covering sheet 4. A pair of non-contracted parts 49 are provided between the both ends of the first middle elastic member 47 and the edges 121 of the pair of leg openings 12 (the pair of non-contracted parts 49 are surrounded by double-dash lines in FIGS. 2 to 4). As shown in FIGS. 3 and 4, both ends of the second middle elastic member 48 are also apart from the edges 121 of the pair of leg openings 12, and a pair of non-contracted parts 49 are provided between the both ends of the second middle elastic member 48 and the edges 121 of the pair of leg openings 12.

As shown in FIGS. 2 to 4, the first middle elastic member 47 is continuous between the pair of non-contracted parts 49 in the middle front part 4022, and the second middle elastic member 48 is continuous between the pair of non-contracted parts 49 in the middle back part 4023, to form continuous middle gathers between each of the pairs of non-contracted parts 49.

In a state where the first sheet 41 and the second sheet 42 of the outer covering sheet 4 are expanded in the absorbent product 1 (see FIG. 4), it is preferable that a length in the horizontal direction of the first middle elastic member 47 is equal to or larger than 40% and equal to or smaller than 80% of a width in the horizontal direction of the middle front part 4022 at a position where the first middle elastic member 47 is provided, and more preferably, the length is equal to or larger than 50% and equal to or smaller than 70% of the width. In this case, the width in the horizontal direction of the middle front part 4022 at the position where the first middle elastic member 47 is provided, is an average width in the horizontal direction of the middle front part 4022 at the portion, and the width is that in the horizontal direction of the middle front part 4022 in the vicinity of a position where a central first middle elastic yarn 471, out of three first middle elastic yarns 471 of the first middle elastic member 47, is provided (the three first middle elastic yarns 471 are discussed later). Also, it is preferable that a length in the horizontal direction of the second middle elastic member 48 is equal to or larger than 40% and equal to or smaller than 80% of an average width in the horizontal direction of the middle back part 4023 at a position where the second middle elastic member 48 is provided, and more preferably, the length is equal to or larger than 50% and equal to or smaller than 70% of the width.

In other words, in the state where the first sheet 41 and the second sheet 42 of the outer covering sheet 4 are expanded in the absorbent product 1, a total width in the horizontal direction of the pair of non-contracted parts 49 in the middle front part 4022 is preferably equal to or larger than 20% and equal to or smaller than 60% of an average width in the horizontal direction of the middle front part 4022 at a position where the pair of non-contracted parts 49 are provided (the average width is equal to that in the horizontal direction at the position where the first middle elastic member 47 is provided, which is discussed above), and more preferably, the total width is equal to or larger than 30% and equal to or smaller than 50% of the average width. Also, a total width in the horizontal direction of the pair of non-contracted parts 49 in the middle back part 4023 is preferably equal to or larger than 20% and equal to or smaller than 60% of an average width in the horizontal direction of the middle back part 4023 at a position where the pair of non-contracted parts 49 are provided (more preferably, equal to or larger than 30% and equal to or smaller than 50%).

In the middle front part 4022, the leg elastic members 44 are not provided in the pair of non-contracted parts 49 as shown in FIG. 2. That is, the leg elastic members 44 are divided into upper portions and a lower portion by the pair of non-contracted parts 49, and portions above the non-contracted parts 49 (i.e., portions on the side of the front part 401) of the leg elastic members 44 are located between the non-contracted parts 49 and the vicinities of lower ends of side end portions of the front part 401, along the edges 121 of the pair of leg openings 12, respectively. A portion below the non-contracted parts 49 (i.e., a portion opposite to the front part 401) of the leg elastic members 44 is located from one non-contracted part 49 to the vicinity of the folded part 4021 along one leg opening 12 and located in the vicinity of the folded part 4021 along the horizontal direction and further, located from the vicinity of the folded part 4021 to the other non-contracted part 49 along the other leg opening 12.

In the middle back part 4023, the leg elastic members 44 are not provided in the pair of non-contracted parts 49 as shown in FIG. 3, similarly to the middle front part 4022 (see FIG. 2), and the leg elastic members 44 are divided into upper portions and a lower portion by the pair of non-contracted parts 49. Portions above the non-contracted parts 49 of the leg elastic members 44 are located between the non-contracted parts 49 and the vicinities of lower ends of side end portions of the back part 403, along the edges 121 of the pair of leg openings 12, respectively. A portion below the non-contracted parts 49 of the leg elastic members 44 is located from one non-contracted part 49 to the vicinity of the folded part 4021 along one leg opening 12 and located in the vicinity of the folded part 4021 along the horizontal direction and further, located from the vicinity of the folded part 4021 to the other non-contracted part 49 along the other leg opening 12.

Therefore, the right and left ends of the front part 401 and the back part 403 of the outer covering sheet 4 shown in FIGS. 2 and 3 are bonded each other and thereby, the leg elastic members 44 are intermittently (discontinuously) positioned around the pair of leg openings 12 in a non-circular shape.

As shown in FIGS. 1 to 4, the waist elastic member 43, the front elastic member 45 and the back elastic member 46, and the first middle elastic member 47 and the second middle elastic member 48 are elastic yarn groups each including elastic yarns which are a plurality of elastic elements. In the absorbent product 1, these elastic yarn groups are collectively called as "the waist elastic member 43", "the front elastic member 45 and the back elastic member 46", and "the first middle elastic member 47 and the second middle elastic member 48", respectively.

A plurality of elastic yarns included in the waist elastic member 43 are separately provided in the front part 401 and the back part 403 of the outer covering sheet 4, as shown in FIG. 4. The right and left ends of the front part 401 and the back part 403 are bonded each other, and the plurality of elastic yarns included in the waist elastic member 43 are thereby positioned along the edge of the waist opening 11 (see FIG. 1) of the absorbent product 1 around the almost whole waist opening 11. The right and left ends of the front part 401 and the back part 403 of the outer covering sheet 4 are bonded each other, and a plurality of elastic yarns included in the front elastic member 45 and a plurality of elastic yarns included in the back elastic member 46 are thereby positioned around the almost whole waist part (i.e., the front part 401 and the back part 403) between the waist opening 11 and the pair of leg openings 12.

In the middle front part 4022 (and the front part 401) of the outer covering sheet 4, three elastic yarns 441 included in the leg elastic members 44 are arranged in the vicinity of each leg opening 12 in nearly parallel with the edge 121 of the leg opening 12, as shown in FIG. 2. In the middle back part 4023 (and the back part 403), three elastic yarns 442 included in the leg elastic members 44 are arranged in the vicinity of each leg opening 12 in nearly parallel with the edge 121 of the leg opening 12, as shown in FIG. 3. In the following description, the elastic yarns 441, 442 are referred to as "front part leg elastic yarns 441" and "back part leg elastic yarns 442", respectively.

As shown in FIG. 2, the first middle elastic member 47 has three first middle elastic yarns 471. Each first middle elastic yarn 471 is continuous between the pair of non-contracted parts 49 in the middle front part 4022 and the first middle elastic yarns 471 are arranged in nearly parallel with the horizontal direction. As shown in FIG. 3, the second middle elastic member 48 has three second middle elastic yarns 481 similarly to the first middle elastic member 47, and each second middle elastic yarn 481 is continuous between the pair of non-contracted parts 49 in the middle back part 4023 and the second middle elastic yarns 481 are arranged in nearly parallel with the horizontal direction.

Examples of the plurality of elastic yarns included in each of the waist elastic member 43, the leg elastic members 44, the front elastic member 45 and the back elastic member 46, and the first middle elastic member 47 and the second middle elastic member 48 shown in FIG. 4, are polyurethane yarn, strip-like polyurethane film, yarn-like or strip-like natural rubber, or the like. In the present preferred embodiment, a plurality of polyurethane yarns which are yarn-like members with a fineness of 300 to 2000 decitex (dtex) are bonded with the first sheet 41 and the second sheet 42 (see FIG. 5) by rubber hot melt adhesive. Bonding methods such as ultrasonic compression bonding and thermo compression bonding can be used for adhering the elastic yarns included in each elastic member with the first sheet 41 and the second sheet 42.

From the view point of simplification of the manufacturing or the like, however, bonding with the hot melt adhesive is preferable.

Figure 6:
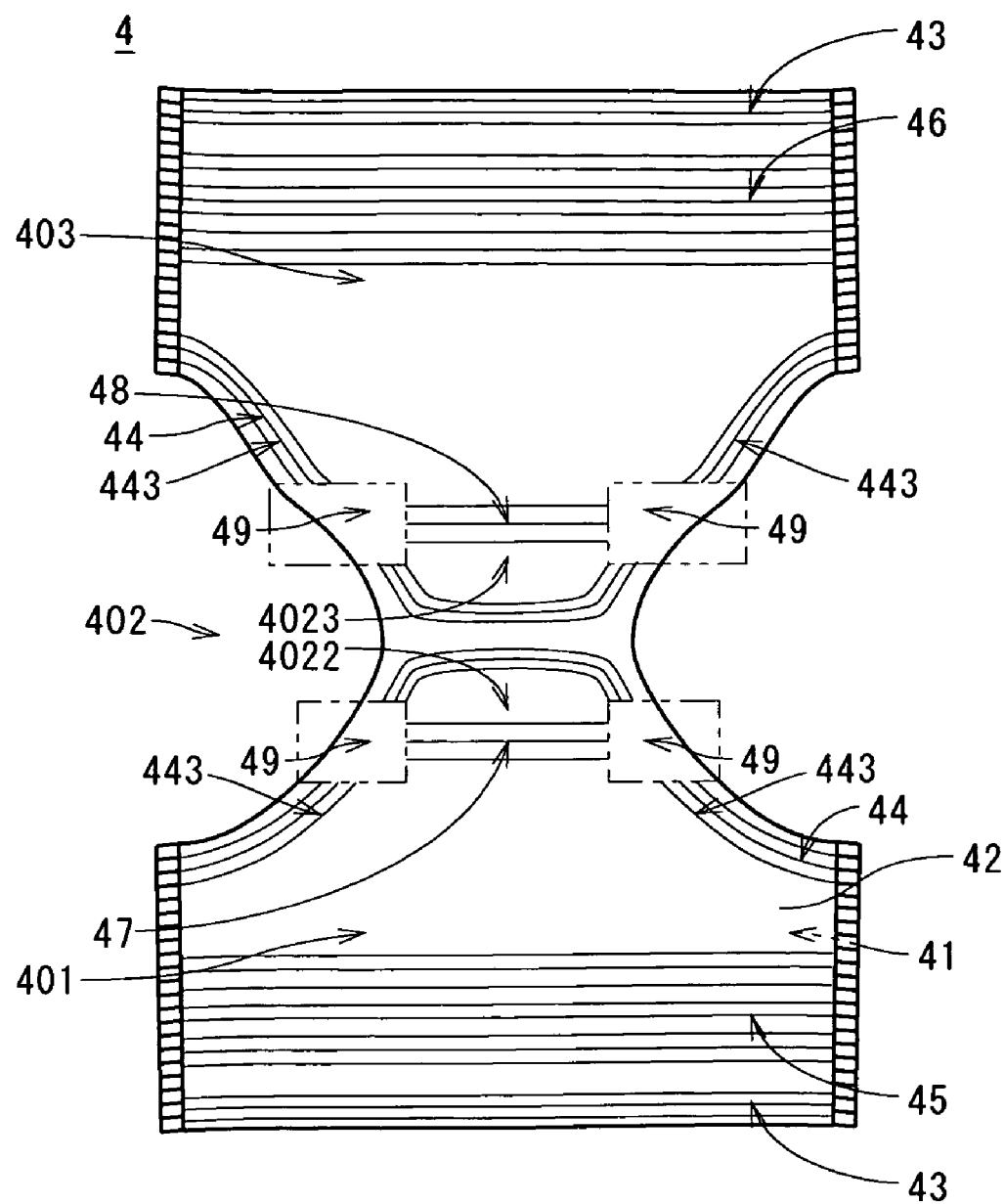
FIG. 6 is a plan view of an outer covering sheet in a state where the outer covering sheet is spread.

FIG. 6 is a plan view of the outer covering sheet 4 as viewed from the wearer's side in a state where the outer covering sheet 4 is spread (i.e., a state where the right and left ends of the front part 401 and the back part 403 are not bonded each other). In the state where the first sheet 41 and the second sheet 42 of the outer covering sheet 4 are expanded as shown in FIG. 6, the waist elastic member 43, the leg elastic members 44, the front elastic member 45 and the back elastic member 46, and the first middle elastic member 47 and the second middle elastic member 48 are respectively extended. In FIG. 6, the waist elastic member 43, the leg elastic members 44, the front elastic member 45 and the back elastic member 46, and the first middle elastic member 47 and the second middle elastic member 48 are shown by thin solid lines for convenience of illustration (the same is applied in FIGS. 7 to 11).

As shown in FIG. 6, the pair of leg elastic members 44 have a pair of inclined parts 443 each of which is inclined relatively to both of the longitudinal direction of the outer covering sheet 4 (i.e., the longitudinal direction is the vertical direction in FIG. 6 and corresponds to the longitudinal direction of the absorbent product 1) and the width direction (i.e., the horizontal direction) perpendicular to the longitudinal direction in each of the middle front part 4022 and the middle back part 4023. The non-contracted part 49 is provided in each of the inclined parts 443.

Figure 7:
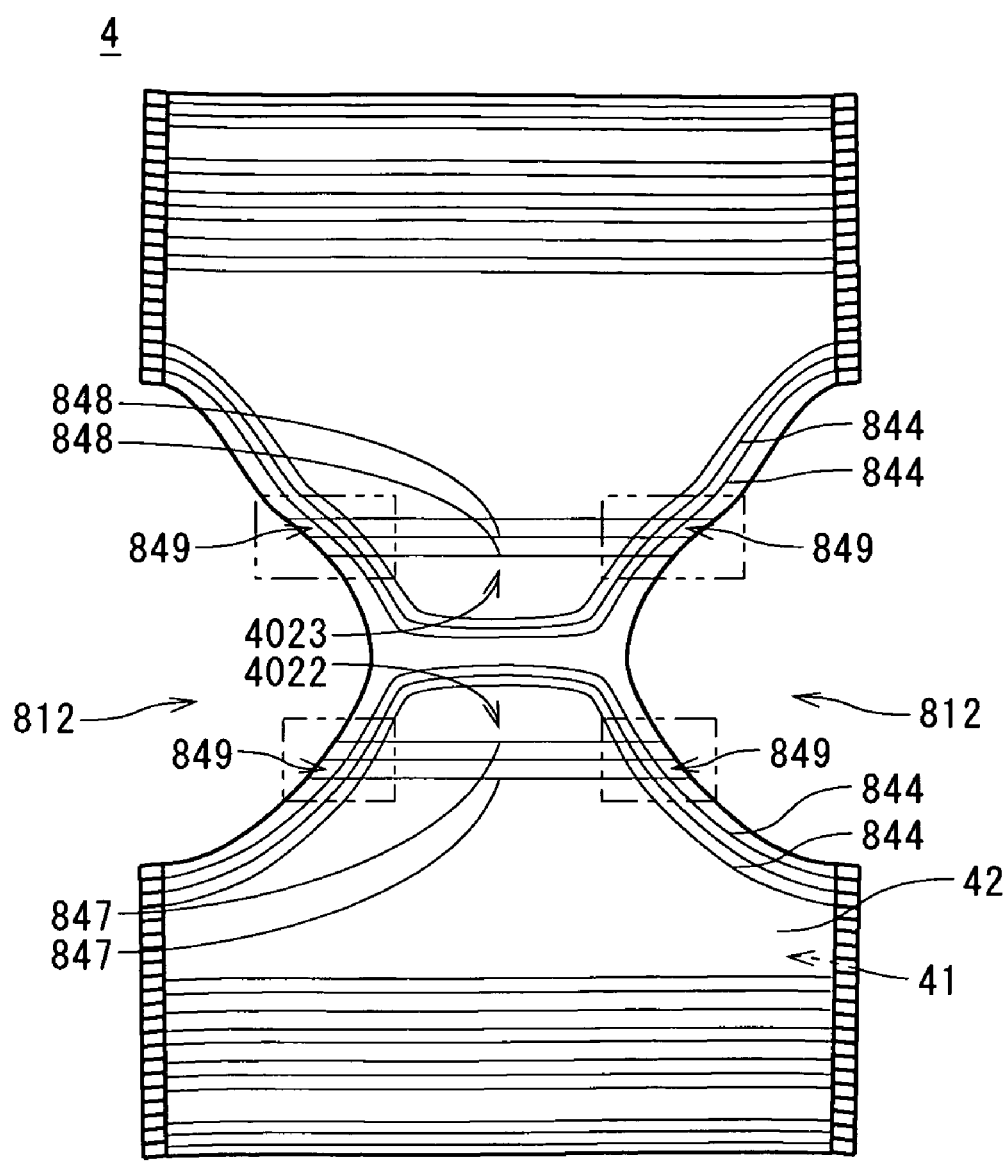
FIG. 7 is a plan view showing the outer covering sheet in the process of manufacturing.

FIG. 7 is a plan view showing the outer covering sheet 4 in the process of manufacturing. As shown in FIG. 7, in formation of the outer covering sheet 4, the hot melt adhesive is applied over the whole surface of the first sheet 41 and/or the second sheet 42 by using a curtain spray or the like, and thereafter, a plurality of extended elastic yarns 844 which are elastic members to be the leg elastic members 44 are bonded with the first sheet 41 and the second sheet 42, passing through portions 849 which are to be the pair of non-contracted parts 49 (i.e., extending from one non-contracted part 849 to the other non-contracted part 849) in each of the middle front part 4022 and the middle back part 4023 (the portions 849 are surrounded by double-dash lines in FIG. 7 and hereinafter simply referred to as "non-contracted parts 849").

In parallel with bonding of the elastic yarns 844, the holt melt adhesive is applied over the whole length of a plurality of elastic yarns 847, 848 which are elastic members to be the first middle elastic member 47 and the second middle elastic member 48, and thereafter, each of the plurality of extended elastic yarns 847, 848 are bonded with (interposed between) the first sheet 41 and the second sheet 42, passing through the pair of non-contracted parts 849 (i.e., extending from one non-contracted part 849 to the other non-contracted part 849) in each of the middle front part 4022 and the middle back part 4023. Thus, the elastic yarns 844 and the elastic yarns 847 cross one another in the pair of non-contracted parts 849 in the middle front part 4022, and the elastic yarns 844 and the elastic yarns 848 cross one another in the pair of non-contracted parts 849 in the middle back part 4023.

In each of the pair of non-contracted parts 849 in the middle front part 4022, the elastic yarns 844 and the elastic yarns 847 crossing one another are cut by a rotary blade having a plurality of blades or the like, together with the first sheet 41 and the second sheet 42, to thereby lose elasticity of portions in the pair of non-contracted parts 849. The leg elastic members 44, the first middle elastic member 47, and the pair of non-contracted parts 49 in the middle front part 4022 are formed as shown in FIG. 2.

Similarly, in each of the pair of non-contracted parts 849 in the middle back part 4023 shown in FIG. 7, the elastic yarns 844 and the elastic yarns 848 crossing one another are cut by the rotary blade having the plurality of blades or the like, together with the first sheet 41 and the second sheet 42, to thereby lose elasticity of portions in the pair of non-contracted parts 849. The leg elastic members 44, the second middle elastic member 48, and the pair of non-contracted parts 49 in the middle back part 4023 are formed as shown in FIG. 3. Pieces of cut elastic yarns 844, 847, 848 contract between the first sheet 41 and the second sheet 42 without contracting the first sheet 41 and the second sheet 42.

Actually, the elastic members (i.e., the elastic yarns 844, 847, 848) to be the leg elastic members 44, the first middle elastic member 47 and the second middle elastic member 48, are bonded with a sheet member which is the continuous first sheets 41 and a sheet member which is the continuous second sheets 42. Cutting of the elastic members is performed to a bonded member of these sheet members (i.e., the bonded member is a sheet member which is a continuous body of the outer covering sheets 4). Notches 812 corresponding to the leg openings 12 are formed after cutting the elastic members.

As discussed above, the first middle elastic member 47 is located along the horizontal direction in the middle front part 4022 of the outer covering sheet 4 in the absorbent product 1, and the first middle elastic member 47 contracts the first sheet 41 and the second sheet 42, to thereby form the middle gathers. With this operation, fitting of the middle part 402 to the wearer can be improved and the appearance of the absorbent product 1 is enhanced. Also in a state where excrement such as urine is absorbed by the absorbent 2, since great expansion of the middle part 402 is suppressed by the middle gathers, it is possible to enhance the appearance of the absorbent product 1 and to surely prevent leak of the excrement from the absorbent product 1.

In the middle front part 4022, the pair of non-contracted parts 49 are provided between the both ends of the first middle elastic member 47 and the edges 121 of the pair of leg openings 12. Therefore, flexibility of portions in the vicinities of the leg openings 12 in the outer covering sheet 4 can be improved by providing the non-contracted parts 49 in the vicinities of the leg openings 12 in the absorbent product 1. As a result, it is possible to prevent portions around the legs of the absorbent product 1 from fitting too tightly to the wearer (i.e., prevent the legs of the wearer from being strongly compressed in the absorbent product 1) and to provide the wearer with comfortable feeling in wearing the absorbent product 1 while preventing leak of excrement. Further, the legs of the wearer can be smoothly inserted into the leg openings 12 in wearing the absorbent product 1, and the wearer can easily wear the absorbent product 1.

In the absorbent product 1, since the second middle elastic member 48 is provided in the middle back part 4023 of the outer covering sheet 4, middle gathers are formed in the middle back part 4023 similarly to the middle front part 4022, and the pair of non-contracted parts 49 are provided between the both ends of the second middle elastic member 48 and the edges 121 of the pair of leg openings 12. As a result, it is possible to further improve fitting of the middle part 402 to the wearer and flexibility of the portions in the vicinities of the leg openings 12 in the outer covering sheet 4.

In the absorbent product 1, the total width of the pair of non-contracted parts 49 in the middle front part 4022 is equal to or larger than 20% (more preferably, equal to or larger than 30%) of the width in the horizontal direction of the middle front part 4022 at the position where the pair of non-contracted parts 49 are provided, to further improve flexibility of the portions in the vicinities of the leg openings 12 in the outer covering sheet 4. The total width is equal to or smaller than 60% (more preferably, equal to or smaller than 50%) of the width in the horizontal direction of the middle front part 4022 at the position where the pair of non-contracted parts 49 are provided, to fully retain the length of the first middle elastic member 47 and further to improve fitting of the middle part 402 to the wearer. The total width of the pair of non-contracted parts 49 in the middle back part 4023 is equal to or larger than 20% and equal to or smaller than 60% (more preferably, equal to or larger than 30% and equal to or smaller than 50%) of the width in the horizontal direction of the middle back part 4023 at the position where the pair of non-contracted parts 49 are provided, to further improve fitting of the middle part 402 to the wearer and flexibility of the portions in the vicinities of the leg openings 12 in the outer covering sheet 4.

In the middle part 402, since the first middle elastic member 47 is continuous between the pair of non-contracted parts 49 in the middle front part 4022, it is possible to increase the strength of the middle gathers by the first middle elastic member 47, and further to improve fitting of the middle part 402 to the wearer. Also, since the second middle elastic member 48 is continuous between the pair of non-contracted parts 49 in the middle back part 4023, it is possible to further improve fitting of the middle part 402 to the wearer.

In manufacturing of the absorbent product 1, the elastic yarns 847 which are bonded with the first sheet 41 and the second sheet 42, passing through the pair of non-contracted parts 49 in the middle front part 4022, are cut in the pair of non-contracted parts 49 to lose elasticity of portions in the pair of non-contracted parts 49, and the first middle elastic member 47 is thereby formed. Thus, it is possible to easily form the outer covering sheet 4 and the absorbent product 1. The elastic yarns 848 which are bonded with the first sheet 41 and the second sheet 42, passing through the pair of non-contracted parts 49 in the middle back part 4023, are cut in the pair of non-contracted parts 49 to lose elasticity of portions in the pair of non-contracted parts 49, and the second middle elastic member 48 is thereby formed. Thus, it is possible to form the outer covering sheet 4 and the absorbent product 1 more easily.

As discussed above, in the absorbent product 1, the elastic yarns 844 which are bonded with the first sheet 41 and the second sheet 42, passing through the pairs of non-contracted parts 49 in the middle front part 4022 and the middle back part 4023, are cut in the pairs of non-contracted parts 49 to lose elasticity of portions in the pairs of non-contracted parts 49, and the pair of leg elastic members 44 are thereby formed. The pair of leg opening gathers are formed by the leg elastic members 44 along the edges 121 of the pair of leg openings 12. In this manner, the leg opening gathers are formed by the leg elastic members 44 which are intermittently located around the pair of leg openings 12 in a non-circular shape, and it is possible to achieve high fitting of the middle part 402 to the wearer and high flexibility of the portions in the vicinities of the leg openings 12 in the outer covering sheet 4.

In manufacturing of the absorbent product 1, the elastic members to be the first middle elastic member 47 and the second middle elastic member 48 and the elastic members to be the leg elastic members 44, are cut in the pairs of non-contracted parts 49 in the middle front part 4022 and the middle back part 4023 with crossing each other, to form the first middle elastic member 47, the second middle elastic member 48 and the leg elastic members 44. As a result, it is possible to simply form the outer covering sheet 4 and the absorbent product 1.

Figure 8:
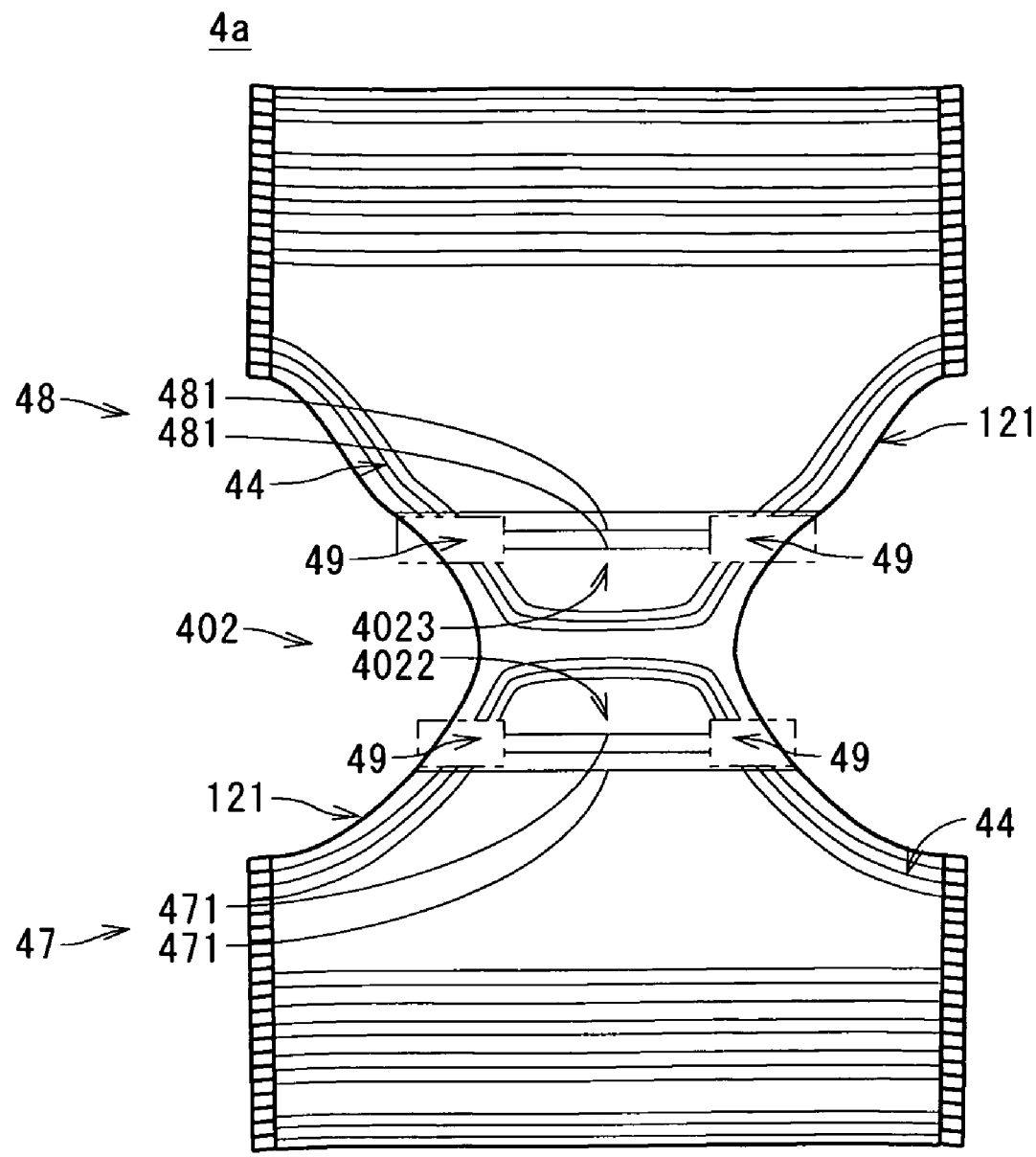
FIG. 8 is a plan view of an outer covering sheet of an absorbent product in accordance with the second preferred embodiment, in a state where the outer covering sheet is spread.

Next discussion will be made on an absorbent product in accordance with the second preferred embodiment of the present invention. FIG. 8 is a plan view of an outer covering sheet 4a of the absorbent product in accordance with the second preferred embodiment, as viewed from the wearer's side in a state where the outer covering sheet 4a is spread. In the outer covering sheet 4a, non-contracted parts 49 are provided in both ends of first middle elastic yarns 471 which are a part (two in the preferred embodiment) of three first middle elastic yarns 471 included in a first middle elastic member 47 in a middle front part 4022 of a middle part 402, as shown in FIG. 8. In a middle back part 4023, non-contracted parts 49 are provided in both ends of second middle elastic yarns 481 which are a part (two in the preferred embodiment) of three second middle elastic yarns 481 included in a second middle elastic member 48. The other constituent elements of the absorbent product according to the second preferred embodiment are the same as those in the absorbent product 1 shown in FIGS. 1 to 6, and they are represented by the same reference signs.

In the middle front part 4022 of the outer covering sheet 4a shown in FIG. 8, both ends of the two first middle elastic yarns 471 included in the first middle elastic member 47 are apart from the edges 121 of the pair of leg openings 12 (see FIGS. 1 to 3), and a pair of non-contracted parts 49 are provided between the both ends of the two first middle elastic yarns 471 and the edges 121 of the pair of leg openings 12. The remaining one first middle elastic yarn 471 included in the first middle elastic member 47 crosses the pair of leg elastic members 44 in the vicinities of the edges 121 of the pair of leg openings 12.

Similarly, in the middle back part 4023 of the outer covering sheet 4a, both ends of the two second middle elastic yarns 481 included in the second middle elastic member 48 are apart from the edges 121 of the pair of leg openings 12, and a pair of non-contracted parts 49 are provided between the both ends of the two second middle elastic yarns 481 and the edges 121 of the pair of leg openings 12. The remaining one second middle elastic yarn 481 included in the second middle elastic member 48 crosses the pair of leg elastic members 44 in the vicinities of the edges 121 of the pair of leg openings 12.

Figure 9:
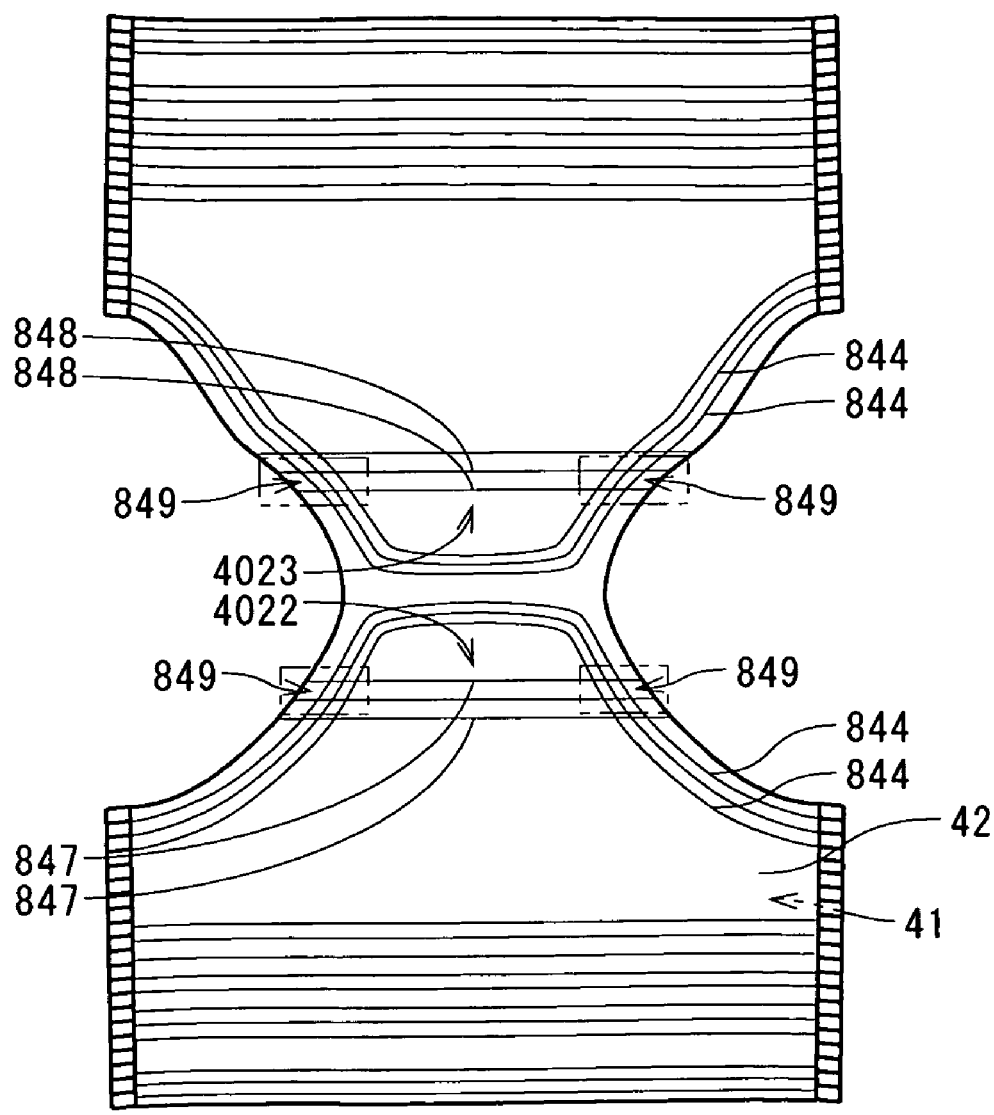
FIG. 9 is a plan view showing the outer covering sheet in the process of manufacturing.

In manufacturing of the outer covering sheet 4a, as shown in FIG. 9, the three elastic yarns 844 and the two elastic yarns 847, out of the plurality of extended elastic yarns bonded with the first sheet 41 and the second sheet 42, are cut in the pair of non-contracted parts 849 in the middle front part 4022 with crossing one another, and the remaining one elastic yarn 847 is not cut. The three elastic yarns 844 and the two elastic yarns 848 are cut in the pair of non-contracted parts 849 in the middle back part 4023 with crossing one another, and the remaining one elastic yarn 848 is not cut.

In the absorbent product according to the second preferred embodiment, middle gathers are formed in the middle part 402 by the first middle elastic member 47 and the second middle elastic member 48 shown in FIG. 8, to improve fitting of the middle part 402 to the wearer similarly to the first preferred embodiment. The pair of non-contracted parts 49 are portions in the vicinities of the leg openings 12 (see FIGS. 1 to 3) in the both ends of the first middle elastic yarns 471 which are at least part of the plurality of first middle elastic yarns 471 included in the first middle elastic member 47 (i.e., the both ends of the first middle elastic yarns 471 are at least partially apart from the pair of leg openings 12, and the pair of non-contracted parts 49 are provided between the both ends of the first middle elastic yarns 471 and the pair of leg openings 12), to thereby improve flexibility of the portions in the vicinities of the leg openings 12 in the outer covering sheet 4a. Further, the pair of non-contracted parts 49 are portions in the vicinities of the leg openings 12 in the both ends of the second middle elastic yarns 481 which are at least part of the plurality of second middle elastic yarns 481 included in the second middle elastic member 48 (i.e., the both ends of the second middle elastic yarns 481 are at least partially apart from the pair of leg openings 12, and the pair of non-contracted parts 49 are provided between the both ends of the second middle elastic yarns 481 and the pair of leg openings 12), to thereby improve flexibility of the portions in the vicinities of the leg openings 12 in the outer covering sheet 4a.

Figure 10:
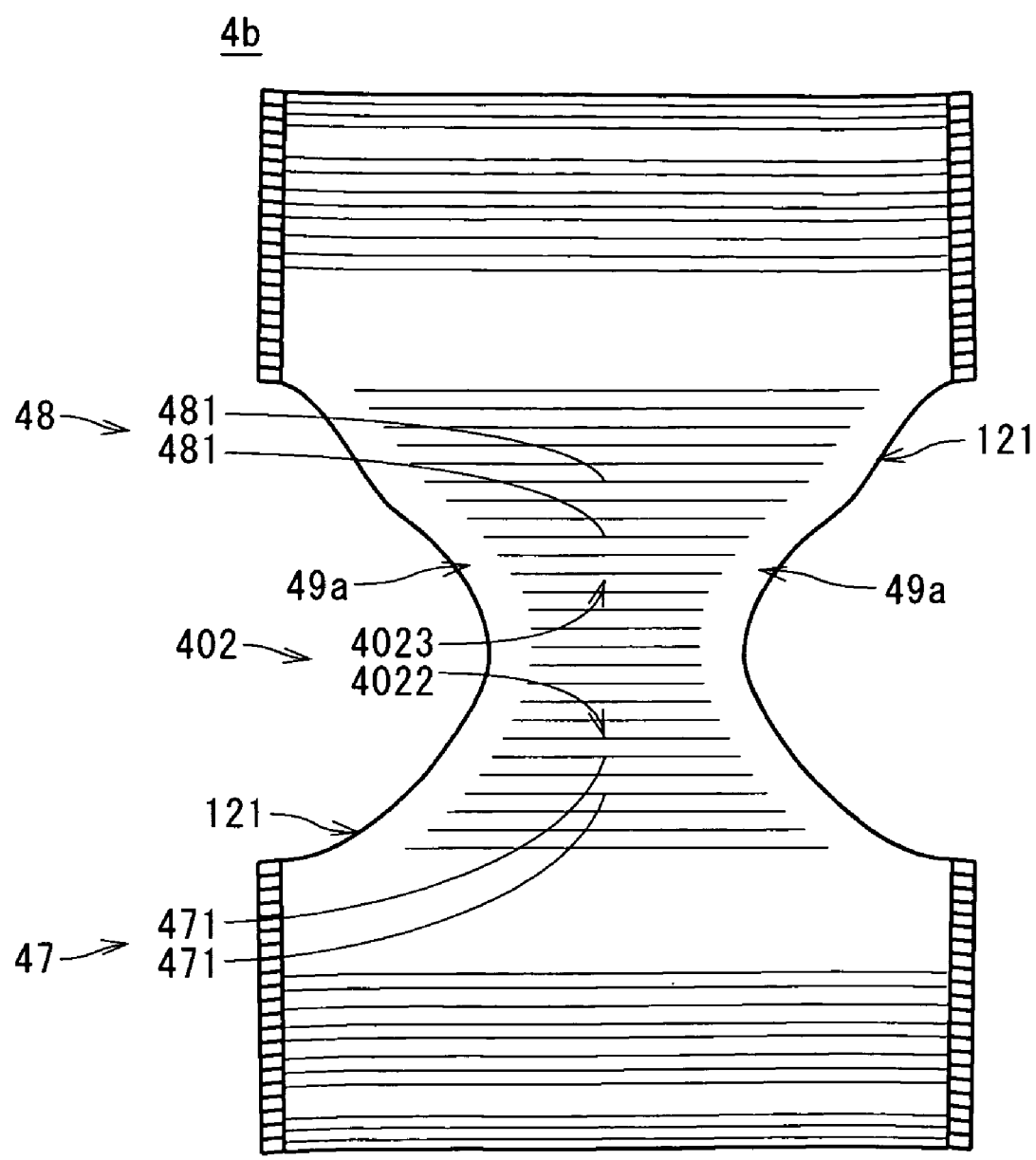
FIG. 10 is a plan view of an outer covering sheet of an absorbent product in accordance with the third preferred embodiment, in a state where the outer covering sheet is spread.

Next, discussion will be made on an absorbent product in accordance with the third preferred embodiment of the present invention. FIG. 10 is a plan view of an outer covering sheet 4b of the absorbent product in accordance with the third preferred embodiment, as viewed from the wearer's side in a state where the outer covering sheet 4b is spread. As shown in FIG. 10, leg elastic members are not provided in portions in the vicinities of the edges 121 of leg openings in the outer covering sheet 4b, and a plurality of first middle elastic yarns 471 and a plurality of second middle elastic yarns 481 (i.e., the first middle elastic member 47 and the second middle elastic member 48) are arranged across the almost whole areas of the middle front part 4022 and the middle back part 4023 in the middle part 402, in nearly parallel with the horizontal direction.

Both ends of the first middle elastic member 47 and both ends of the second middle elastic member 48 are apart from the edges 121 of a pair of leg openings, and a pair of non-contracted parts 49a are provided between the both ends of the first middle elastic member 47 and the edges 121 of the pair of leg openings and between the both ends of the second middle elastic member 48 and the edges 121. In the outer covering sheet 4b according to the third preferred embodiment, it is possible to improve fitting of the middle part 402 to the wearer and flexibility of the portions in the vicinities of the leg openings of the outer covering sheet 4b, similarly to the first preferred embodiment.

Figure 11:
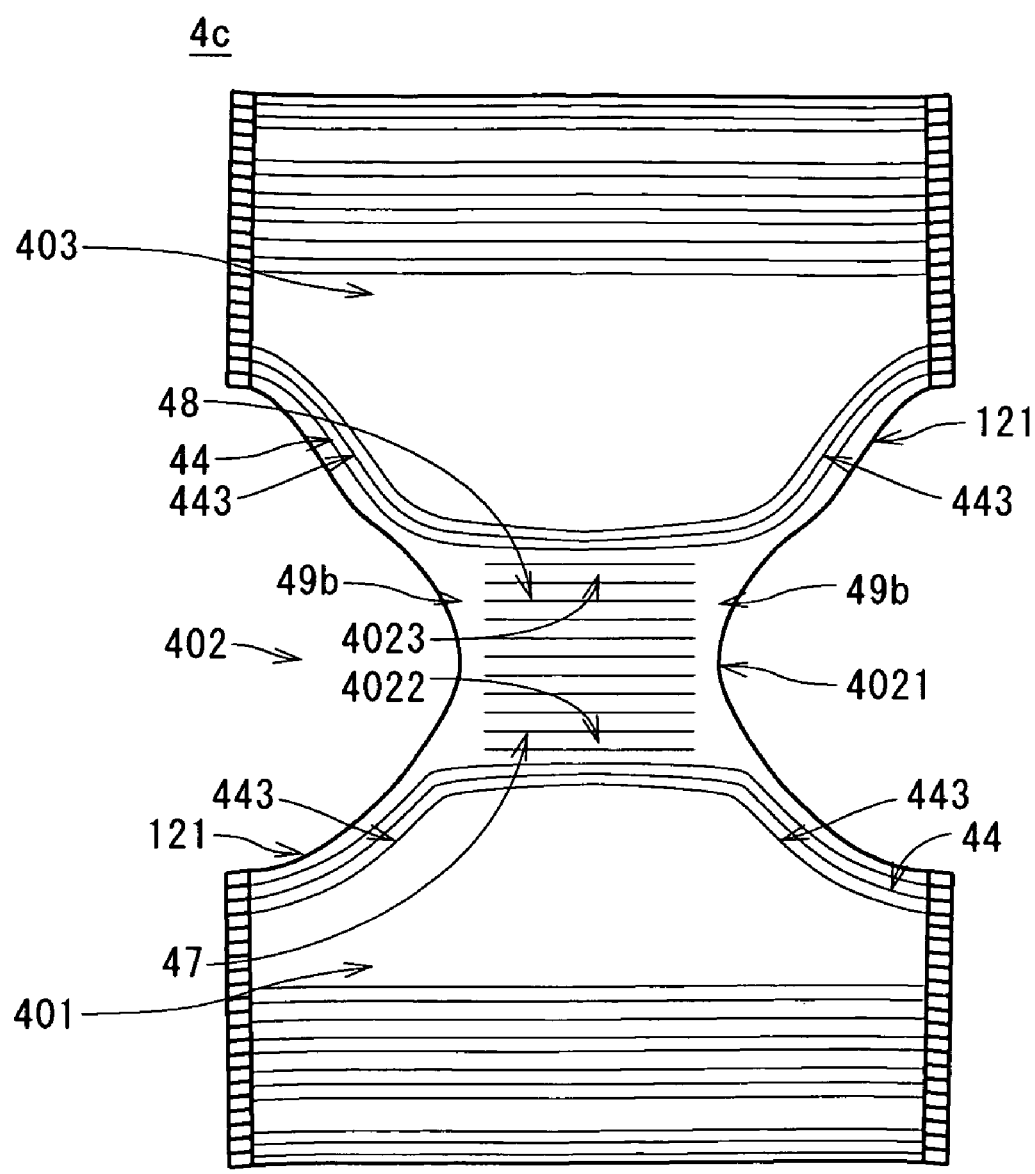
FIG. 11 is a plan view of an outer covering sheet of an absorbent product in accordance with the fourth preferred embodiment, in a state where the outer covering sheet is spread.

Next, discussion will be made on an absorbent product in accordance with the fourth preferred embodiment of the present invention. FIG. 11 is a plan view of an outer covering sheet 4c of the absorbent product in accordance with the fourth preferred embodiment, as viewed from the wearer's side in a state where the outer covering sheet 4c is spread. As shown in FIG. 11, in the outer covering sheet 4c, the leg elastic members 44 are located on the side of the front part 401 in the middle front part 4022 of the middle part 402 and the side of the back part 403 in the middle back part 4023, and portions between the pair of inclined parts 443 (i.e., portions which are nearly parallel with the horizontal direction) of the leg elastic members 44 are located in the vicinity of the central portion in the longitudinal direction of the middle front part 4022 or the middle back part 4023. In the outer covering sheet 4c, the leg elastic members 44 are continuously provided in the horizontal direction of the outer covering sheet 4c without being cut by the blades.

The first middle elastic member 47 and the second middle elastic member 48 are arranged between the leg elastic members 44 in the middle front part 4022 and the leg elastic members 44 in the middle back part 4023 (i.e., in the vicinity of the folded part 4021), without crossing the leg elastic members 44. Both ends of the first middle elastic member 47 and both ends of the second middle elastic member 48 are apart from the edges 121 of a pair of leg openings, and a pair of non-contracted parts 49b are provided between the both ends of the first middle elastic member 47 and the edges 121 of the pair of leg openings and between the both ends of the second middle elastic member 48 and the edges 121. In the outer covering sheet 4c according to the fourth preferred embodiment, it is possible to improve fitting of the middle part 402 to the wearer and flexibility of the portions in the vicinities of the leg openings of the outer covering sheet 4c, similarly to the first preferred embodiment.

Though the preferred embodiments of the present invention have been discussed above, the present invention is not limited to the above-discussed preferred embodiments, but allows various variations.

In manufacturing of the absorbent products according to the first and second preferred embodiments, the elastic yarns 844, 847, 848 are not necessarily cut with the first sheet 41 and the second sheet 42 but may be cut with at least one of the first sheet 41 and the second sheet 42. Thus, it is possible to easily form the absorbent product. Cutting of the elastic yarns 844, 847, 848 may be performed, e.g., by blow of compressed air or by making blades having blunt edges come into contact with the outer covering sheet 4 and then applying ultrasonic wave to the outer covering sheet 4, without cutting the first sheet 41 and the second sheet 42.

In manufacturing of the absorbent products according the above preferred embodiments, the first middle elastic member 47 and the second middle elastic member 48 are not necessarily formed by cutting the elastic yarns 847, 848 in the non-contracted parts 49. For example, there may be a case where the hot melt adhesive is not applied to the portions to be the non-contracted parts 49 of the first sheet 41 and the second sheet 42 and the portions corresponding to the non-contracted parts 49 of the elastic yarns 847, 848, the hot melt adhesive is only applied to a portion other than the portions corresponding to the non-contracted parts 49 of the elastic yarns 847, 848, and then the elastic yarns are bonded with the first sheet 41 and the second sheet 42 and are cut on right and left sides of the outer covering sheet 4. With this operation, portions of the elastic yarns where the hot melt adhesive is not applied, contract toward the central side in the horizontal direction without contracting the first sheet 41 and the second sheet 42, and portions of the elastic yarns where the hot melt adhesive is applied, contract together with the first sheet 41 and the second sheet 42 to form middle gathers.

In the absorbent product 1 according to the first preferred embodiment, each of the first middle elastic member 47 and the second middle elastic member 48 may have only one elastic yarn, or may have two or four elastic yarns or more. Also in this case, it is possible to improve fitting of the middle part 402 to the wearer and flexibility of the portions in the vicinities of the leg openings 12 in the outer covering sheet 4.

In the absorbent products according to the above preferred embodiments, the first middle elastic yarns 471 and the second middle elastic yarns 481 of the first middle elastic member 47 and the second middle elastic member 48 are not necessarily arranged in nearly parallel with the horizontal direction, as long as the first middle elastic yarns 471 and the second middle elastic yarns 481 are arranged along the horizontal direction. For example, the first middle elastic yarns 471 and the second middle elastic yarns 481 may be arranged to curve toward the folded part 4021 of the middle part 402 in the vicinity of the central portion in the horizontal direction. One of the first middle elastic member 47 and the second middle elastic member 48 may be provided in the middle part 402 of the outer covering sheet 4 in the absorbent product. In this case, the middle gathers and the pair of non-contracted parts 49 are formed in one of the middle front part 4022 and the middle back part 4023.

The non-contracted parts in the absorbent product do not need to completely lose elasticity but may be portions which are substantially regarded as not having elasticity since their elasticity is obviously small as compared to the other portions with elasticity where elastic members are located in the outer covering sheet (e.g., portions where the leg opening gathers are formed).

While the invention has been shown and described in detail, the foregoing description is in all aspects illustrative and not restrictive. It is therefore understood that numerous modifications and variations can be devised without departing from the scope of the invention.

This application claims priority benefit under 35 U.S.C. Section 119 of Japanese Patent Application No. 2007-143494 filed in the Japan Patent Office on May 30, 2007, the entire disclosure of which is incorporated herein by reference.

What is claimed is:

1. A pants-type absorbent product which has a waist opening at an upper end and a pair of leg openings on a lower part, said absorbent product comprising:
    an outer covering sheet having a front part to be positioned on a stomach side of a wearer, a back part to be positioned on a back side of a wearer, and a middle part between said front part and said back part, said outer covering sheet being folded in said middle part such that said middle part is lower than said front part and said back part, right and left ends of said front part being bonded to right and left ends of said back part, respectively, to form a waist opening at upper ends of said front part and said back part and a pair of leg openings on right and left sides of said middle part; and
    an absorbent which is attached on an inner side of said outer covering sheet to absorb excrement from said wearer,
    wherein said outer covering sheet comprises:
    (i) a first sheet;
    (ii) a second sheet which is laminated on said first sheet to be bonded with said first sheet;
    (iii) a middle elastic member interposed between said first sheet and said second sheet in said middle part, said middle elastic member extending straight from one leg opening to the other leg opening, and contracting said first sheet and said second sheet to form middle gathers; and
    (iv) leg elastic members which are located along edges of said pair of leg openings, respectively, said leg elastic members contracting to form a pair of leg opening gathers,
    wherein both ends of said middle elastic member are spaced apart from said pair of leg openings,
    wherein a pair of non-contracted parts are provided between said both ends of said middle elastic member and said pair of leg openings, and
    wherein each of said leg elastic members extends around substantially an entire circumference of a respective one of said leg openings, except for said non-contracted parts.

2. The absorbent product according to claim 1, wherein said middle elastic member has a plurality of elastic yarns, and
    said both ends of said middle elastic member are constituted by ends of said plurality of elastic yarns.

3. The absorbent product according to claim 2, wherein said plurality of elastic yarns are formed by cutting both end portions of at least part of extended elastic yarns, which are bonded with said first sheet and said second sheet, together with at least one of said first sheet and said second sheet, to lose elasticity of said both end portions in said pair of non-contracted parts.

4. The absorbent product according to claim 3,
    wherein said leg elastic members are formed by cutting extended elastic members, which are bonded with said first sheet and said second sheet, together with at least one of said first sheet and said second sheet, to lose elasticity of portions in said pair of non-contracted parts.

5. The absorbent product according to claim 4, wherein said at least part of extended elastic yarns to be at least part of said middle elastic member and said extended elastic members to be said leg elastic members are arranged crossing each other at said pair of non-contracted parts and are cut at said pair of non-contracted parts.

6. The absorbent product according to claim 2, wherein a total width in a horizontal direction of said pair of non-contracted parts is at least 20% and not greater than 60% of a width in said horizontal direction of said middle part at a position where said pair of non-contracted parts are provided, in a state where said outer covering sheet is expanded.

7. The absorbent product according to claim 2, wherein said middle elastic member is continuous between said pair of non-contracted parts.

8. The absorbent product according to claim 2, wherein said middle elastic member is located between said front part and a folded part which is a lower end of said middle part,
    wherein another middle elastic member is located between said back part and said folded part of said middle part,
    wherein said another middle elastic member is interposed between said first sheet and said second sheet in said middle part, extends from said one leg opening to said other leg opening, and contracts said first sheet and said second sheet to form middle gathers,
    wherein both ends of said another middle elastic member are spaced apart from said pair of leg openings, and
    wherein another pair of non-contracted parts are provided between said both ends of said another middle elastic member and said pair of leg openings.

9. The absorbent product according to claim 1, wherein said middle elastic member is formed by cutting both end portions of at least part of an extended elastic member which is bonded with said first sheet and said second sheet, together with at least one of said first sheet and said second sheet, to lose elasticity of said both end portions in said pair of non-contracted parts.

10. The absorbent product according to claim 9,
    wherein said leg elastic members are formed by cutting extended elastic members, which are bonded with said first sheet and said second sheet, together with at least one of said first sheet and said second sheet, to lose elasticity of portions in said pair of non-contracted parts.

11. The absorbent product according to claim 10, wherein said extended elastic member to be said middle elastic member and said extended elastic members to be said leg elastic members are arranged crossing each other at said pair of non-contracted parts and are cut at said pair of non-contracted parts.

12. The absorbent product according to claim 1, wherein a total width in a horizontal direction of said pair of non-contracted parts is at least 20% and not greater than 60% of a width in said horizontal direction of said middle part at a position where said pair of non-contracted parts are provided, in a state where said outer covering sheet is expanded.

13. The absorbent product according to claim 1, wherein said middle elastic member is continuous between said pair of non-contracted parts.

14. The absorbent product according to claim 1, wherein said middle elastic member is located between said front part and a folded part which is a lower end of said middle part,
wherein another middle elastic member is located between said back part and said folded part of said middle part,
wherein said another middle elastic member is interposed between said first sheet and said second sheet in said middle part, extends from said one leg opening to said other leg opening, and contracts said first sheet and said second sheet to form middle gathers,
wherein both ends of said another middle elastic member are spaced apart from said pair of leg openings, and
wherein another pair of non-contracted parts are provided between said both ends of said another middle elastic member and said pair of leg openings.

15. The absorbent product according to claim 1, wherein said middle elastic member extends straight in a first direction from one of said non-contracted parts to the other of said non-contracted parts, and
wherein said leg elastic members extend from said non-contracted parts, respectively, in directions oblique to the first direction.

16. The absorbent product according to claim 1, wherein both ends of said middle elastic member are disposed between said leg openings and between said leg elastic members.

17. The absorbent product according to claim 1, wherein said non-contracted parts are disposed on said circumferences of said leg elastic members, and
wherein each of said leg elastic members extends around an entire circumference of said respective one of said leg openings, except for said non-contracted parts.

18. The absorbent product according to claim 1, wherein both ends of said middle elastic member are disposed at said non-contracted parts.

19. The absorbent product according to claim 1, wherein both ends of said middle elastic member are disposed between said leg openings and between said leg elastic members,
wherein said non-contracted parts are disposed on said circumferences of said leg elastic members,
wherein each of said leg elastic members extends around an entire circumference of said respective one of said leg openings, except for said non-contracted parts, and
wherein both ends of said middle elastic member are disposed at said non-contracted parts.

* * * * *